United States Patent
Flanders et al.

(10) Patent No.: US 7,230,710 B2
(45) Date of Patent: Jun. 12, 2007

(54) POLARIZATION CONTROLLING FIBER PROBE FOR SEMICONDUCTOR SOURCE SPECTROSCOPY SYSTEM

(75) Inventors: Dale C. Flanders, Lexington, MA (US); Walid A. Atia, Lexington, MA (US); Mark E. Kuznetsov, Lexington, MA (US)

(73) Assignee: Axsun Technologies, Inc., Billerica, MA (US)

( * ) Notice: Subject to any disclaimer, the term of this patent is extended or adjusted under 35 U.S.C. 154(b) by 303 days.

(21) Appl. No.: 11/018,687

(22) Filed: Dec. 21, 2004

(65) Prior Publication Data

US 2006/0132782 A1   Jun. 22, 2006

(51) Int. Cl.
*G01N 21/00* (2006.01)
(52) U.S. Cl. .................................................... 356/432
(58) Field of Classification Search .................. None
See application file for complete search history.

(56) References Cited

U.S. PATENT DOCUMENTS

| | | | | |
|---|---|---|---|---|
| 3,991,383 | A * | 11/1976 | Hughes | 372/20 |
| 6,040,914 | A * | 3/2000 | Bortz et al. | 356/435 |
| 6,212,033 | B1 * | 4/2001 | Sasaki | 360/230 |
| 6,339,603 | B1 * | 1/2002 | Flanders et al. | 372/20 |
| 2001/0052979 | A1 | 12/2001 | Treado et al. | |
| 2003/0007523 | A1 | 1/2003 | Chapman et al. | |
| 2004/0246490 | A1 * | 12/2004 | Wang | 356/479 |
| 2006/0152729 | A1 * | 7/2006 | Drennen et al. | 356/432 |

FOREIGN PATENT DOCUMENTS

EP    1 345 294 A2    9/2003

OTHER PUBLICATIONS

Ranaswamy et al. ("Single-Polarization Optical Fibers: Exposed Cladding Technique" by V. Ranaswamy, I. P. Kaminow and P. Kaiser in Applied Physics Letters, vol. 33, p. 814 (1978).*
U.S. Appl. No. 10/688,690, filed Oct. 17, 2003, Atia et al.
U.S. Appl. No. 10/953,043, filed Sep. 29, 2004, Flanders et al.

* cited by examiner

*Primary Examiner*—Gregory J. Toatley, Jr.
*Assistant Examiner*—Jonathan Skovholt
(74) *Attorney, Agent, or Firm*—Houston Eliseeva LLP

(57) ABSTRACT

A semiconductor source spectroscopy system controls optical power variation of the tunable signal due to polarization dependent loss in the system and thus improves the noise performance of the system. It relies on using polarization control between the source and the sample and/or the sample and the detector. In one example, the source has a semiconductor optical amplifier and an intracavity tunable element for generating a tunable optical signal for illuminating a sample. The tunable optical signal is spectrally tuned over a scan band of the spectroscopy system by operation of the intracavity tunable element.

10 Claims, 1 Drawing Sheet

POLARIZATION CONTROLLING FIBER PROBE FOR SEMICONDUCTOR SOURCE SPECTROSCOPY SYSTEM

BACKGROUND OF THE INVENTION

Most spectroscopy systems fall into one of two categories. They can be tunable source systems that generate a wavelength tunable optical signal that is scanned over a wavelength scan band. A detector is then used to detect the tunable optical signal after interaction with the sample. The time response of the detector corresponds to the spectral response of the sample. Such systems are typically referred to as pre-dispersive. Alternatively, a tunable detector system can be used. In this case, a broadband optical signal is used to illuminate the sample. Then, signal from the sample is passed through an optical bandpass filter, which is tuned over the scan band such that a detector time response is used to resolve the sample's spectrum. Such systems are typically referred to as post-dispersive.

Between tunable source and tunable detector systems, tunable source systems have some advantages. They can have a better response for the same optical power transmitted to the sample. That is, tunable detector systems must illuminate the sample with a broadband signal that covers the entire scan band. Sometimes, this can result in excessive sample heating and power consumption at the source, making the system inefficient. In contrast, at any given instant, tunable source systems only generate and illuminate the sample with a very narrow band within the scan band.

Further, tunable source systems have advantages associated with detection efficiency. Relatively large detectors can be used to capture a larger fraction of the light that may have been scattered by or transmitted through the sample, since there is no need to capture light and then collimate the light for transmission through a tunable filter or to a grating, for example.

A number of general configurations are used for tunable source spectroscopy systems. The lasers have advantages in that very intense tunable optical signals can be generated. A different configuration uses the combination of a broadband source and a tunable passband filter, which generates the narrowband signal that illuminates the sample.

Historically, most tunable lasers were based on solid state or liquid dye gain media. While often powerful, these systems also have high power consumptions. Tunable semiconductor laser systems have the advantage of relying on small, efficient, and robust semiconductor sources. One configuration uses semiconductor optical amplifiers (SOAs) and microelectromechanical system (MEMS) Fabry-Perot tunable filters, as described in U.S. Pat. No. 6,339,603, by Flanders, et al., which is incorporated herein by this reference in its entirety. In other examples, intra cavity gratings are used to tune the laser emission.

In commercial examples of the broadband source/tunable filter source configuration, the tunable filter is an acousto-optic tunable filter (AOTF) and the broadband signal is generated by a diode array or tungsten-halogen bulb, for example. More recently, some of the present inventors have proposed a tunable source that combines edge-emitting, superluminescent light emitting diodes (SLEDs) and MEMS Fabry-Perot tunable filters to generate the tunable optical signal. See US2005/0083533A1, U.S. patent application Ser No. 10/688,690, filed on Oct. 17, 2003, by Atia, et at., which is incorporated herein by this reference in its entirety. The MEMS device is highly stable, can handle high optical powers, and can further be much smaller and more energy-efficient than typically large and expensive AOTFs. Moreover, the SLEDS can generate very intense broadband optical signals over large bandwidths, having a much greater spectral brightness than tungsten-halogen sources, for example.

SUMMARY OF THE INVENTION

Moving from standard diode arrays and tungsten-halogen bulbs to edge-emitting devices such as superluminescent light emitting diodes (SLED), other edge emitting diodes including lasers, and semiconductor optical amplifiers (SOA) has the advantage that higher optical powers can be achieved.

One characteristic of these edge-emitting semiconductor devices such as SLEDs, diode lasers, and SOAs is that they tend to be highly polarization anisotropic, however. This is due to the nature of the semiconductor gain medium. Current is usually injected from a top electrode through a quantum well structure to the bottom electrode. Thus, the gain medium is not circularly symmetric around the optical axis and thus light from these devices is usually highly polarized. Most often, it emits light in only a single polarization.

Even vertical surface emitting laser (VCEL) devices, where the gain region is more symmetric, tend to be highly polarized. This is because invariably one of the polarization modes encounters more loss so that other so that the device runs in the other mode. In fact, it is common to fabricate the devices so that there is a strong preference for one of the modes to remove uncertainly as to in which mode the device operates.

For some applications, polarization isotropic semiconductor optical amplifiers have been produced. These are most common in telecom applications where polarization dependent loss (PDL) is metric for characterizing the quality of this class of devices. However, in order to obtain this polarization isotropy, typically trade-offs must be made in terms of the output power, device gain, and/or the bandwidth of operation.

These trade-offs, necessitating lower optical power and narrower band, are contrary to the typical requirements for a spectroscopy system, however. Scan band and power should be maximized in order to improve the performance of the system. Thus, for most spectroscopy applications, polarization anisotropic semiconductor gain elements are often used.

Thus, the broadband signal or the tunable signal that is transmitted to the sample is highly polarized unless a polarization diversity scheme is used requiring multiple sources with orthogonal polarizations or a polarization scrambler is employed. Both these solutions, however, are expensive because they necessitate multiple sources that operate in tandem with polarization control between the sources or a separate polarization scrambler, which usually also has a high insertion loss.

A problem arises, however, for applications requiring a high signal-to-noise operation, when the source is highly polarized. Often, the optical link between the tunable signal or broadband signal source and the sample and between the sample and the detector has substantial PDL. Moreover, this PDL may be dynamic over time especially in response to mechanical vibration or other changes to the fiber links or other optical elements in the path between the source and sample and from the sample to the detector. This PDL, in view of the highly polarized nature of the light from these semiconductor sources, can introduce spectral distortion in the measured signal and can detrimentally impact the signal-to-noise ratio and thus spectral performance of these systems.

As a result, the present invention is directed to a semiconductor source spectroscopy system. It is applicable to systems that use broadband sources, tunable sources, and tunable detector systems. It relies on using polarization control between the source and the sample and/or the sample and the detector.

In general, according to one aspect, the invention features a semiconductor spectroscopy system. It comprises a semiconductor source and polarization controlling fiber in the link between the semiconductor source and the detector.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
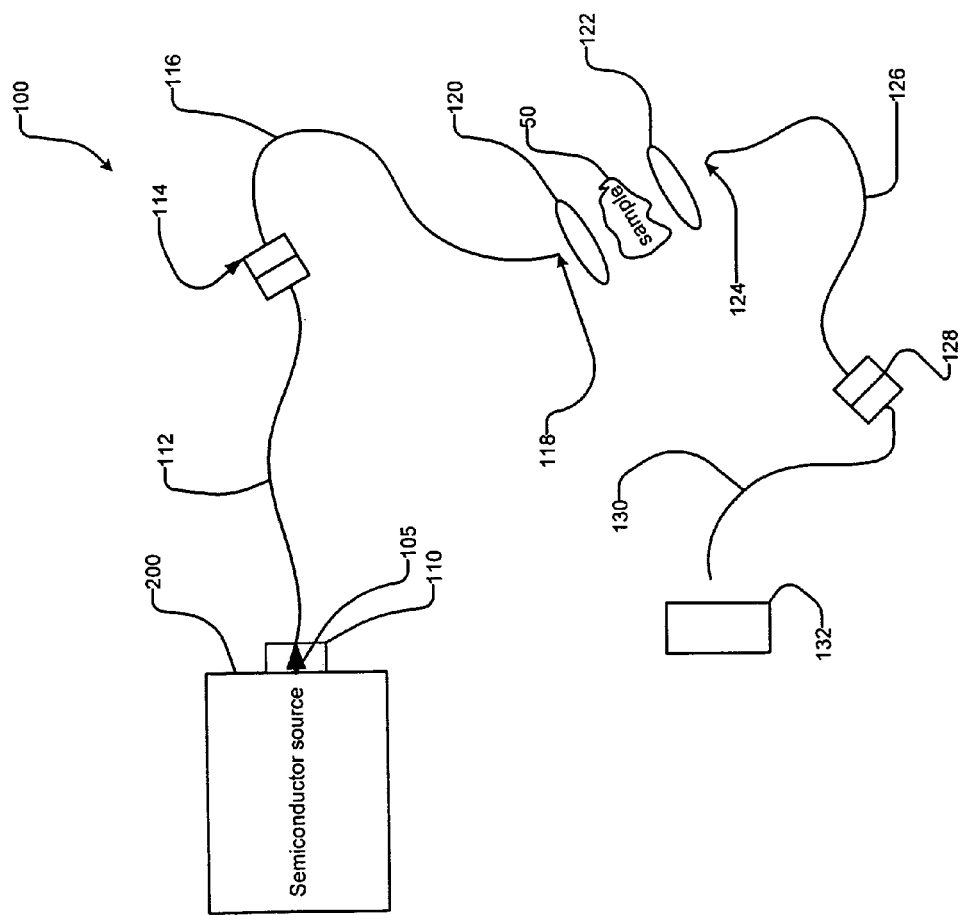
FIG. 1 is a schematic view of a tunable source semiconductor spectroscopy system with a fiber link having polarization control.

FIG. 1 illustrates a semiconductor source spectroscopy system 100, which has been constructed according to the principles of the present invention.

Specifically, the system 100 comprises a semiconductor source 200. In one example, this semiconductor source is a source as described in US2005/0083533A1, U.S. patent application Ser. No. 10/688,690, filed Oct. 17, 2003, which is incorporated herein by reference in its entirety. In other examples, it comprises a semiconductor source as described in US2006/0072632A1, U.S. patent application Ser. No. 10/953,043, filed on Sep. 29, 2004, entitled "Semiconductor Laser with Tilted Fabry-Perot Tunable Filter" by Dale C. Flanders, et at., which is also incorporated herein by this reference in its entirety. In other examples, semiconductor source is a laser system in which the laser tuning element is a movable grating, such as a Littrow configuration.

In other examples, the semiconductor source 200, rather than generating a tunable optical signal, generates a broadband signal. In this case, the semiconductor source comprises an edge emitting light emitting diode device. In one example, the semiconductor source comprises a superluminescent light emitting diode. In other examples, the source 200 comprises a standard edge emitting semiconductor laser or vertical surface emitting laser diode. In these examples, the system is often current or thermally tuned.

As a result, the signal 105, being either a broadband signal or a tunable signal, is generated by the semiconductor source 200 and is highly polarized. Typically, it is has only substantially a single polarization.

For example, light from the semiconductor source 200 can have a polarization extinction ratio (PER), that is ratio of powers in the two polarizations, of 10-25 dB. The present invention is applicable to these highly polarized source. More generally, the present invention is also applicable to less polarized sources since even a small PDL for a low PER source can introduce noise and impact the signal to noise ratio (SNR) of the spectroscopy system.

This signal 105 travels through, for example, a coupler 110 and a length of fiber 112, in one example.

It further travels through another coupler 114 that connects the fiber pigtail 112 from the source 200 to another length of fiber or fiber pigtail 116 that connects or carries the optical signal 105 to the sample 50, in some examples.

The sample optical fiber length 116 extends in the illustrated example from the connector 114 to the pigtail's end 118. Here, the semiconductor source signal, being again either a broadband signal or a tunable signal is often columnated by, for example, a source-side lens element 120 for transmission to the sample 50.

Further, sample-side lens 122 may be used to capture the signal from the sample 50 and couple it into another sample-side optical fiber 126, through endface 124.

Other couplers may be used, such as coupler 128, to connect the sample-side fiber length 126 to a detector optical fiber length 130. The signal is then directed to the detector 132.

In the case where the semiconductor source 200 is a tunable source, the detector 132 is usually a standard detector. In other examples, the detector 132 may be a tunable detector, especially where the semiconductor source 120 produces a broadband signal. Specifically, in one example it is a tunable detector spectroscopy system as disclosed in US2005/0083533A1, U.S. patent application Ser. No. 10/688,690 filed Oct. 17, 2003. In still further examples, it can be a grating-based detector system that has a grating to disperse the broadband signal to an array detector.

It should be noted that the specific nature of the source 200 and the detector 132 is not critical. Instead, the invention is relevant to semiconductor sources, and specifically semiconductor sources that generate highly polarized broadband or tunable signals. The relevance of the detector is that it may be polarization anisotropic, having a certain degree of PDL.

The invention addresses PDL in these various components between the semiconductor source 200 and the detector 132. Specifically, the source side connector 114 and the sample side detector 132 may have different polarization characteristics and specifically polarization dependent loss. Moreover, the PDL for these detectors may vary with the spectrum. The source side lens 120 and the detector side lens 122 can further have PDL. Moreover, the fiber end faces 118 and 124 may further have PDL problems.

According to the invention, the fiber used between the semiconductor source 200 and the detector 132 is polarization controlling fiber. As a result, in one embodiment, the first source side fiber pigtail 112 and the second source side fiber pigtail 116 are constructed from polarization controlling fiber. Moreover, the sample side pigtail 126 and the detector side pigtail 130 are preferably comprised of polarization controlling fiber. However, in other examples, only one or a few of these pigtails is polarization controlling fiber.

The notion is that by using even some polarization controlling fiber between the semiconductor source 200 and the detector 132, polarization dependent loss (PDL) in the optical link and the components is managed since the polarization and thus PLD is stable with time and does not vary during scanning.

Generally, however, because of the nature of the sample, it is most important that the source side pigtails 112 and 116 are polarization controlling fiber and at least one of these is polarization controlling fiber.

Various types of polarization controlling fiber can be used. The most common type of polarization controlling fiber is polarization maintaining (PM) fiber, such as PANDA fiber. Here, the orthogonal polarization modes of the fiber have different propagation constants, which decouples the two polarizations on propagation and thus stabilizes and maintains the polarization distribution. In other examples, single polarization fiber or polarization stripping fiber is used. In these examples, the fiber only propagates a single polarization mode either because of the construction of the fiber, or the insertion of the components that remove light that is polarized along one of the axis.

While this invention has been particularly shown and described with references to preferred embodiments thereof, it will be understood by those skilled in the art that various changes in form and details may be made therein without departing from the scope of the invention encompassed by the appended claims.

What is claimed is:

1. A semiconductor source spectroscopy system, comprising:
   a tunable semiconductor source comprising a semiconductor optical amplifier and an intracavity tunable element for generating a tunable optical signal for illuminating a sample, the tunable optical signal being spectrally tuned over a scan band of the spectroscopy system by operation of the intracavity tunable element;
   a detector for detecting a signal from a sample generated by the illumination of the sample by the tunable optical signal of the semiconductor source; and
   polarization controlling fiber in the optical link between the semiconductor source and the detector.

2. A system as claimed in claim 1, wherein the polarization controlling fiber is polarization maintaining fiber.

3. A system as claimed in claim 1, wherein the polarization controlling fiber is optical fiber that propagates only a single polarization.

4. A system as claimed in claim 1, wherein the intracavity tunable element is a Fabry-Perot tunable filter.

5. A system as claimed in claim 1, wherein the intracavity tunable element is a microelectromechanical Fabry-Perot tunable filter.

6. A system as claimed in claim 1, wherein the intracavity tunable element is a grating.

7. A spectroscopy method, comprising:
   generating a highly polarized tunable optical signal for illuminating a sample using a tunable semiconductor source comprising a semiconductor optical amplifier and an intracavity tunable element;
   transmitting the highly polarized tunable optical signal through a first polarization controlling fiber pigtail;
   coupling the highly polarized tunable optical signal from the first polarization controlling fiber pigtail to a second polarization controlling fiber pigtail;
   illuminating a sample with the highly polarized tunable optical signal from the second polarization controlling fiber pigtail;
   detecting a signal from the sample generated by the illumination of the sample by highly polarized tunable optical signal from the semiconductor source to determined a spectral response of the sample.

8. A system as claimed in claim 1, wherein the polarization controlling fiber comprises a first polarization controlling fiber pigtail from tunable semiconductor source.

9. A system as claimed in claim 8, wherein the polarization controlling fiber further comprises a second polarization controlling fiber pigtail for transmitting the tunable optical signal, which was received from the first polarization controlling fiber pigtail, to the sample.

10. A system as claimed in claim 9, further comprising a fiber coupler for coupling the first polarization controlling fiber pigtail to the second polarization controlling fiber pigtail.

* * * * *